United States Patent [19]
Jarl

[11] Patent Number: 5,954,760
[45] Date of Patent: Sep. 21, 1999

[54] HELICAL WINDING FOR A CARDIAC LEAD

[75] Inventor: Per Jarl, Järfälla, Sweden

[73] Assignee: Pacesetter AB, Solna, Sweden

[21] Appl. No.: 09/073,477

[22] Filed: May 6, 1998

[30] Foreign Application Priority Data

May 7, 1997 [SE] Sweden ................................. 9701719

[51] Int. Cl.⁶ ...................................................... A61N 1/05
[52] U.S. Cl. ......................................................... 607/122
[58] Field of Search ..................................... 607/115, 116, 607/118, 119, 122; 600/373, 374; 174/69, 109, 126.3

[56] References Cited

U.S. PATENT DOCUMENTS

| | | | |
|---|---|---|---|
| 1,987,794 | 1/1935 | Phillips | 174/109 |
| 3,803,344 | 4/1974 | Hemming et al. | 174/109 |
| 3,946,727 | 3/1976 | Okada et al. . | |
| 4,198,991 | 4/1980 | Harris | 607/122 |
| 5,362,113 | 11/1994 | Thomas . | |
| 5,423,881 | 6/1995 | Breyen et al. . | |
| 5,456,707 | 10/1995 | Giele . | |
| 5,609,622 | 3/1997 | Soukup et al. | 607/122 |

FOREIGN PATENT DOCUMENTS

| | | | |
|---|---|---|---|
| 0 092 798 | 11/1983 | European Pat. Off. . | |
| 2919-379 | 11/1980 | Germany | 174/109 |
| 63-264328 | 11/1988 | Japan . | |
| 63-264329 | 11/1988 | Japan . | |

*Primary Examiner*—William E. Kamm
*Assistant Examiner*—George R. Evanisko
*Attorney, Agent, or Firm*—Hill & Simpson

[57] ABSTRACT

A helical winding formed by a wound ribbon and having a length considerably exceeding its diameter, is adapted for implantation into a patient's body. Adjacent turns of the winding partially overlap each other and overlapping portions of the ribbon engage each other to limit the relative axial motion of adjacent turns. At least a portion of the overlapping structure is oriented non-parallel to the longitudinal axis of the winding. In a method of manufacturing such a winding a ribbon is formed to a desired cross-sectional shape with a longitudinally expanding engagement structure. The ribbon is then wound on a mandrel to produce a winding of desired length, with adjacent turns partially overlapping each other and the engagement structure causing overlapping portions of the ribbon to be mechanically engaged so as to limit the relative axial motion of adjacent turns of the winding. Finally the mandrel is removed out of the wound winding. An implantable heart stimulator has a lead employing such a winding provided with an electrode pole at a distal end portion and a connector at the proximal end of the winding for connection to a pulse generator. A surgical tool employs such a winding with the distal end of the winding being provided with a cutting edge and the proximal end with a manipulator for displacing and rotating the winding.

10 Claims, 3 Drawing Sheets

5,954,760

HELICAL WINDING FOR A CARDIAC LEAD

BACKGROUND OF THE INVENTION

1. Field of the Invention

The present invention relates to a helical winding, of the type formed by a band or ribbon in a wound arrangement having a length considerably exceeding its diameter, the winding being adapted for implantation into a patient's body, as well as to a method of manufacturing such a winding of the type including the steps of winding the band or ribbon on a mandrel to obtain a winding of desired length and removing the mandrel from the wound winding, and to an implantable heart stimulator and a surgical tool employing such a winding.

2. Description of the Prior Art

A helical winding of the type described above is known from U.S. Pat. No. 5,423,881, which discloses a medical electrical lead having a conducting wire wound in a helical configuration. The lead is intended for use for endocardial stimulation by an implantable heart pacemaker and includes an electrode at the distal end of the lead and a connector at the proximal end.

This kind of winding has to be flexible to make introduction into e.g. a vein of a patient possible, and a problem with such flexible windings is that a specified length of the winding cannot be maintained during implantation and explantation. Especially in connection with explantation the winding is easily extended (uncoiled). Another disadvantage of this type of winding is a low torsion stiffness.

In U.S. Pat. No. 5,456,707 a pacing lead in the form of a helical winding is disclosed, the torsion characteristics of which are improved by providing an increased stiffness of an intermediate length of the lead. This increased stiffness is obtained by shrinking a tubing of Teflon® over the intermediate section of the lead winding, or by a suitable coating sprayed onto the winding to restrict its flexibility, or by a tube which is force fit between the conductor and inner diameter of the lead outer casing. This tube has a thickness so as to provide minimum clearance with the winding to prevent outward expansion of the winding, i.e. to increase the stiffness of the winding. These special measures for increasing the stiffness of the winding, however, complicate the manufacture of the lead and raises its price.

European Application 0 092 798 shows a multi-pole coaxial circuit intended to be used as an electrode for electric stimulation of body tissue. The circuit has at least one conductor in the form of a helically wound metal ribbon for reducing the diameter of the lead and improving its flexibility. This construction still does not solve the problem of extension of the winding, especially in connection with explantation of the lead, nor the problem of poor torsion stiffness.

SUMMARY OF THE INVENTION

It is an object of the present invention to provide a helical winding, which is flexible enough to make implantation into a patient's body possible as well as explantation therefrom, the elongation of which can be reliably specified, and which is torsion stable.

This object is accomplished in accordance with the invention in a helical winding of the type initially described wherein adjacent turns of the winding partially overlap each other, with the ribbon being wound such that the overlapping portions of the ribbon mechanically engage each other to limit the relative axial motion of adjacent turns. The mechanically engaging structure of the ribbon includes at least one portion of the ribbon which is oriented non-parallel to a longitudinal axis of the winding. Thus a certain relative mobility is allowed between adjacent turns of the winding according to the invention to give the winding the necessary flexibility, because the overlapping portions of the ribbon are provided with a non-planar engaging structure which limits the relative motion of adjacent turns, the length of the winding arrangement can only vary within specified limits, i.e. the elongation of the winding can be specified. The torsion stiffness is also improved and this stiffness is successively increased as the winding is rotated in one predetermined direction, since the turns are partially overlapping.

In an embodiment of the winding 1 according to the invention the cross-section of the ribbon has the shape of two V-forms oppositely directed away from the general plane through the ribbon, each V-form having one shaped shank or leg formed of a common mid-portion of the ribbon. In this embodiment the flexibility of the winding is a result of the flexibility of the material of the ribbon and possibly the result of a minor relative sliding of the overlapping portions.

According to another embodiment of the winding of the invention, the ribbon is made of an electrically conducting material. The winding is then suitable for use as conductor of an electrode lead for a heart stimulator. For this application the winding is normally enclosed in an outer casing. A winding according to the invention made of a ribbon of electrically conducting material also can be used as an effective shield against electromagnetic disturbances for an electrical conductor extending inside the winding.

In another embodiment of the invention a surgical tool has a winding as specified above, the distal end of the winding being provided with a cutting edge and the proximal end of the winding with a manipulable (handheld) mechanism for displacing and rotating the winding. Such a surgical tool can be used e.g. in connection with explantation of an electrode. The winding is then introduced over the implanted lead such that the cutting edge reaches the position where the electrode has tissue ingrowth, whereupon the tool is rotated such that the electrode is cut loose. The winding also can be designed as a combined surgical tool and conductor or shield of an electrode lead. In this case a winding provided with a cutting edge is implanted as a conductor or a shield and at the time of explantation the winding can be cut loose from the heart tissue simply by rotating it.

DESCRIPTION OF THE PREFERRED EMBODIMENTS

Figure 1:
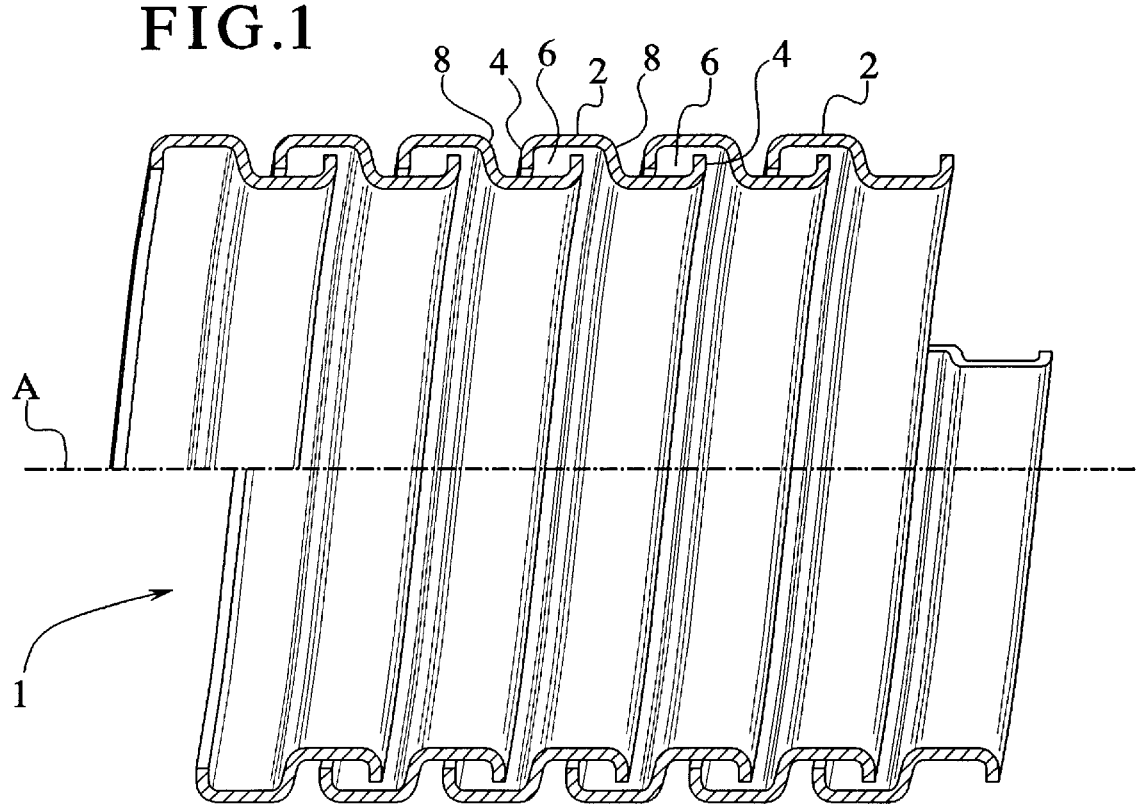
FIG. 1 is a longitudinal sectional view of a portion of a winding arrangement constructed in accordance with the principles of the present invention.
Figure 2:
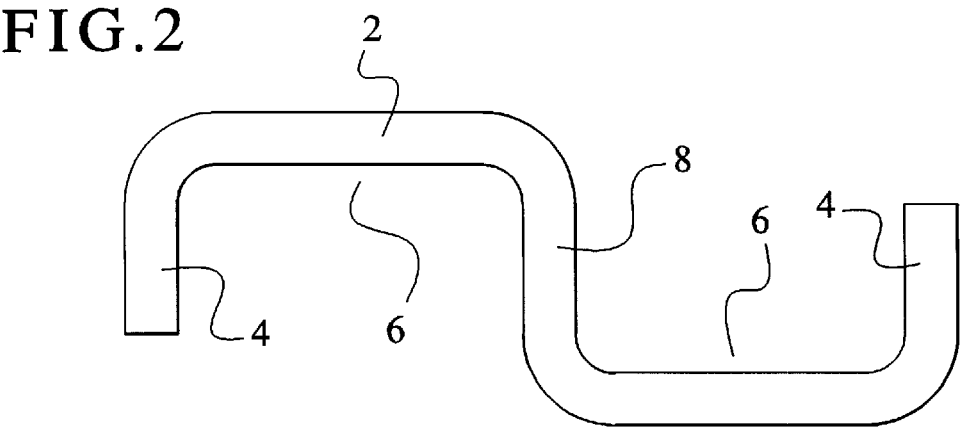
FIG. 2 schematically shows an enlarged detail of the cross-section of one turn of the winding of FIG. 1.

FIG. 1 shows a longitudinal section through a winding arrangement 1 according to the invention, formed by a ribbon 2 having (in the embodiment of FIG. 1) an S-shaped cross-section, cf. FIG. 2. Adjacent turns of the winding arrangement 1 partially overlap, such that the upstanding (free) edge portions 4 of the S-shaped ribbon 2 of one turn are positioned inside the "valleys" 6 inside the corresponding edge portions 4 of adjacent turns. In this configuration adjacent turns can be moved in the axial direction of the winding (i.e., along its longitudinal axis A) relative each other through a small distance corresponding to the width of the valley 6, which is limited by an edge portion and an upstanding mid-portion 8 of the turn in question. This relative mobility of the winding turns make the winding flexible, and compression and elongation of the winding are limited by the engagement of an edge portion 4 of one flight with a mid-portion 8 and an edge portion 4 of an adjacent flight of the turns in the winding.

Figure 9:
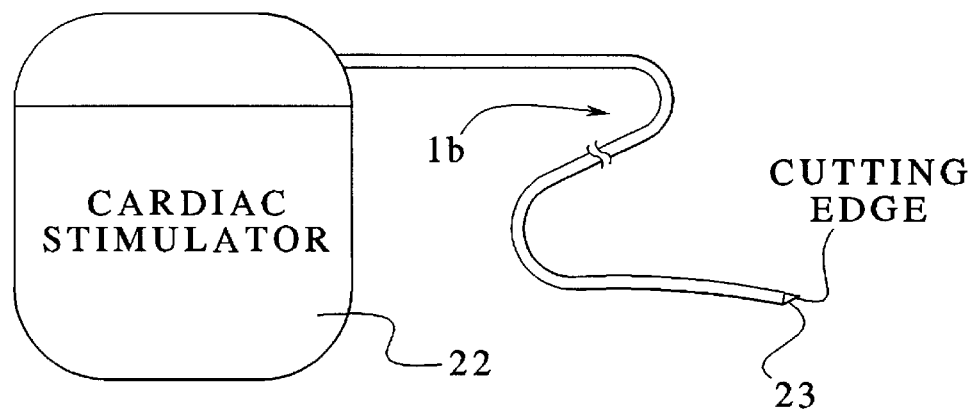
FIG. 9 is a schematic illustration of a cardiac stimulator having a lead employing a winding constructed in accordance with the principles of the present invention.

If the winding arrangement 1 is wound of an electrically conducting material, like a metal, the winding arrangement 1 can be used, as shown in FIG. 9, as a pacing lead 1b for the connection of a cardiac stimulator 22 such as a pacemaker to a patient's heart. The winding arrangement 1 is then preferably enclosed in an outer casing of insulating material, forming the lead 1b.

Figure 7:
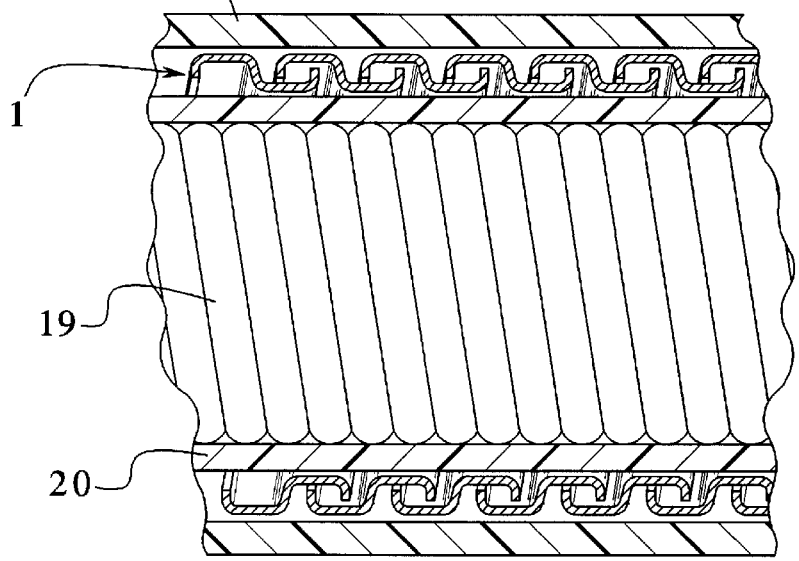
FIG. 7 is a partly sectional view of a portion of an embodiment of the winding of the invention, with an electrical conductor contained therein.

Such an electrically conducting winding can also be used as a shield against electromagnetic disturbances for a conductor 19 extending inside the winding arrangement 1. Such protection against disturbance signals is of importance for certain applications. A partly sectional view of a portion of such a combination is shown in FIG. 7 with an exterior insulating sleeve 18 and an interior insulating sleeve 20 between the winding arrangement 1 and the conductor 19.

Figure 8:
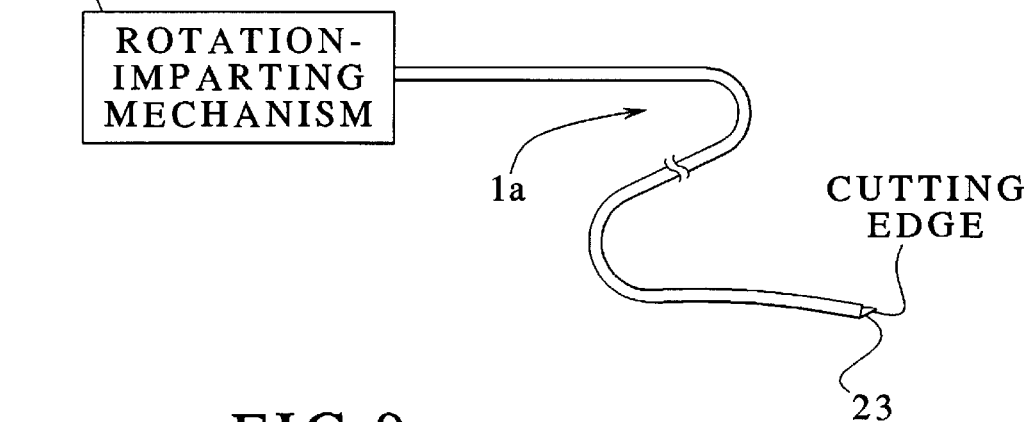
FIG. 8 is a schematic illustration of a surgical instrument employing a winding constructed in accordance with the principles of the present invention.

The winding arrangement 1 according to the invention also exhibits an increased torsion stiffness and since the winding is formed of partially overlapping turns this torsion stiffness is successively increased as the winding arrangement 1 is rotated in one specific direction. This rotation (as well as further manipulation of the winding arrangement 1a can be accomplished by a handheld rotation imparting mechanism, as shown in FIG. 8. Because of this increased torsion stiffness the winding according to the invention can also be used in a surgical tool by providing a cutting edge 23 at the distal end of the winding arrangement 1a. Such a surgical tool can be used when explanting an implanted electrode lead for cutting loose the tip of the lead when it has grown onto body tissue. The winding arrangement 1b is then moved over the implanted lead till the cutting edge 23 reaches the location of the tip of the implanted lead.

Also in the case of using the winding in e.g. a pacing lead 1 b the distal end of the winding can be provided with a cutting edge 23 (as shown in FIG. 9) which makes it possible to cut the lead loose by itself for e.g. explantation by displacing and/or rotating the winding arrangement 1 within the lead 1b.

In FIGS. 3–6 alternative cross-sectional shapes of the winding band are shown.

Figure 3:
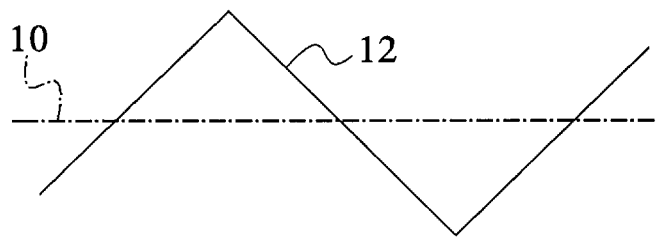
FIGS. 3, 4, 5, and 6 are schematic illustrations showing further embodiments of the cross-section of one turn of a winding in accordance with the invention, respectively.

FIG. 3 shows a saw-toothed cross-sectional shape of the ribbon having V-forms oppositely directed away from the general plane through the ribbon. One of the legs of each V-form is formed by a common mid-portion 12 of the ribbon. In this embodiment the flexibility of the winding arrangement 1 is obtained as a result of the flexibility in the material of the ribbon and possibly due to a small sliding of the overlapping portions of adjacent turns of the winding arrangement 1 relative each other.

Figure 4:
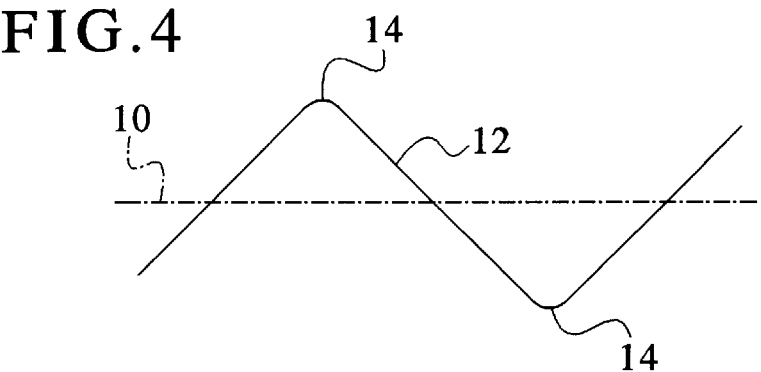
Figure 5:
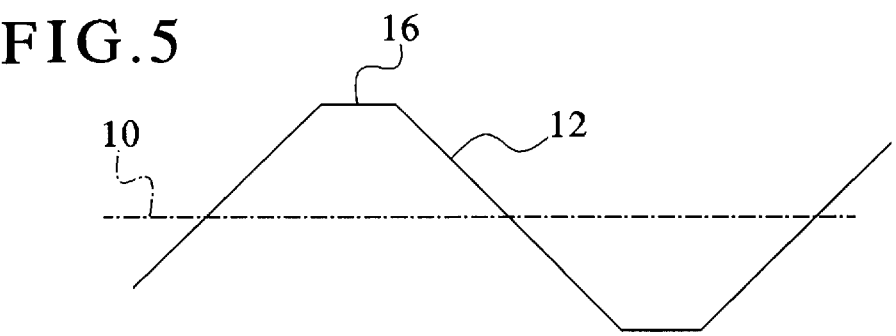

FIGS. 4 and 5 show variations of the ribbon shape in FIG. 3, with rounded tops 14 of the V-forms (FIG. 4) and with the tops of the V-forms cut parallel to the general plane 10 through the ribbon (FIG. 5).

Figure 6:
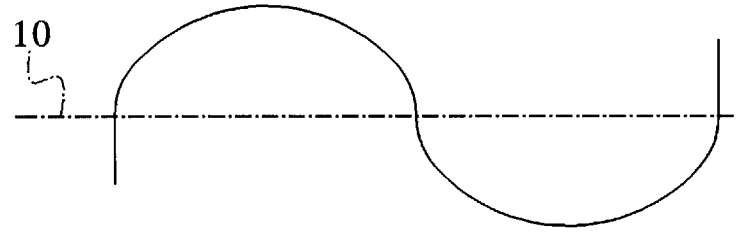

In FIG. 6 another alternative of the cross-sectional shape of the ribbon is shown. In this embodiment the cross-section of the ribbon exhibits a sinusoidal elliptic shape.

Other cross-sectional shapes of the ribbon are possible, such as e.g. an ordinary sinusoidal shape. The only condition which has to be fulfilled is that the cross-sectional shape of the ribbon must be such that overlapping portions of the ribbon engage each other to limit the relative axial motion of adjacent turns of the winding arrangement 1, with at least a portion of the overlapping structure being oriented non-parallel to the longitudinal axis of the winding arrangement 1 (i.e., the axis A in FIG. 1).

When manufacturing the winding according to the invention, a ribbon or a flat wire of a suitable material, like a metal, is formed to the desired cross-sectional shape with longitudinally extending engagement structure as specified above. The ribbon is then wound on a mandrel to produce a winding arrangement 1 of desired axial length and the mandrel is removed out of the winding arrangement 1. The ribbon is wound with adjacent turns partially overlapping each other and the engagement structure is formed such that engaged overlapping portions of the ribbon limit the relative axial motion of adjacent turns of the manufactured winding arrangement 1, in the manner described above.

After being terminated the winding can be enclosed in an outer sleeve 18 of e.g. a polymeric material.

Although modifications and changes may be suggested by those skilled in the art, it is the intention of the inventor to embody within the patent warranted hereon all changes and modifications as reasonably and properly come within the scope of his contribution to the art.

I claim as my invention:

1. A cardiac stimulator comprising:

a winding arrangement having a longitudinal axis, said winding arrangement comprising an electrical conductive ribbon having a plurality of adjacent turns encircling said longitudinal axis said winding arrangement having a longitudinal length and a diameter with said longitudinal length substantially exceeding said diameter and said winding arrangement having first and second opposite ends;

said adjacent turns of said ribbon partially overlapping each other with an overlapping structure having at least a portion oriented non-parallel to said longitudinal axis, said overlapping structure allowing limited relative axial movement along said longitudinal axis of said adjacent turns;

an insulating sleeve surrounding an exterior of said winding arrangement;

a pulse generator electrically connected to said first end of said winding arrangement;

a conductive electrode electrically connected to said second end of said winding arrangement; and said winding arrangement, said pulse generator and said electrode being adapted for implantation in a living subject.

2. A cardiac stimulator as claimed in claim 1 wherein said overlapping structure comprises means for allowing a maximum axial motion of said adjacent winding turns which is less than half of a width of said ribbon.

3. A cardiac stimulator as claimed in claim 1 wherein said ribbon comprises two adjacent channels, each channel having an open side with said open sides facing in opposite directions.

4. A cardiac stimulator as claimed in claim 3 wherein said ribbon has a cross-section comprising two generally U-shaped forms, each U-form having two legs including a commonly shared leg at a mid-portion of said ribbon.

5. A cardiac stimulator as claimed in claim 3 wherein said ribbon has an S-shaped cross-section.

6. A cardiac stimulator as claimed in claim 3 wherein said ribbon has a cross-section comprising two generally V-shaped forms, each V-form having two legs and said two V-forms sharing a leg in a common mid-portion of said ribbon.

7. A cardiac stimulator as claimed in claim 6 wherein each of said V-forms has a top, the respective tops of V-forms being rounded.

8. A cardiac stimulator as claimed in claim 6 wherein each of said V-forms has a top, the respective tops of V-forms being flattened.

9. A cardiac stimulator as claimed in claim 3 wherein said ribbon has a sinusoidal cross-section.

10. A cardiac stimulator as claimed in claim 9 wherein said ribbon has a sinusoidal elliptic cross-section.

\* \* \* \* \*